(12) United States Patent
Jeon et al.

(10) Patent No.: US 10,045,944 B2
(45) Date of Patent: Aug. 14, 2018

(54) PHARMACEUTICAL COMPOSITION CONTAINING CLOMIPRAMINE AND PREPARATION METHOD THEREFOR

(71) Applicant: CTC BIO, INC., Seoul (KR)

(72) Inventors: Hong Ryeol Jeon, Gyeonggi-do (KR); Bong-Sang Lee, Gyeonggi-do (KR); Seong-Shin Kwak, Gyeonggi-do (KR); Dong-Jin Lee, Gyeonggi-do (KR); Hyun-Jung Park, Gyeonggi-do (KR); Jung-Hwa Kim, Gyeonggi-do (KR)

(73) Assignee: CTC BIO, INC., Seoul (KR)

( * ) Notice: Subject to any disclaimer, the term of this patent is extended or adjusted under 35 U.S.C. 154(b) by 0 days.

(21) Appl. No.: 15/109,198

(22) PCT Filed: Dec. 29, 2014

(86) PCT No.: PCT/KR2014/012969
§ 371 (c)(1),
(2) Date: Jun. 30, 2016

(87) PCT Pub. No.: WO2015/102337
PCT Pub. Date: Jul. 9, 2015

(65) Prior Publication Data
US 2016/0324789 A1 Nov. 10, 2016

(30) Foreign Application Priority Data
Dec. 31, 2013 (KR) .................. 10-2013-0168702

(51) Int. Cl.
| | | |
|---|---|---|
| *A61K 9/28* | (2006.01) | |
| *A61K 9/48* | (2006.01) | |
| *A61K 31/519* | (2006.01) | |
| *A61K 31/55* | (2006.01) | |
| *A61K 9/20* | (2006.01) | |
| *A61K 9/16* | (2006.01) | |
| *A61K 9/50* | (2006.01) | |

(52) U.S. Cl.
CPC .......... *A61K 9/4808* (2013.01); *A61K 9/1623* (2013.01); *A61K 9/1635* (2013.01); *A61K 9/1652* (2013.01); *A61K 9/1694* (2013.01); *A61K 9/2018* (2013.01); *A61K 9/2027* (2013.01); *A61K 9/2077* (2013.01); *A61K 9/2095* (2013.01); *A61K 9/28* (2013.01); *A61K 9/5084* (2013.01); *A61K 31/519* (2013.01); *A61K 31/55* (2013.01); *A61K 9/1611* (2013.01)

(58) Field of Classification Search
CPC ...... A61K 9/28; A61K 9/1611; A61K 9/1623; A61K 9/1635; A61K 9/1652; A61K 9/1694; A61K 9/2018; A61K 9/2027; A61K 9/2077; A61K 9/2095; A61K 9/4808; A61K 9/5084; A61K 31/55; A61K 31/519; A61K 2300/00
See application file for complete search history.

(56) References Cited

U.S. PATENT DOCUMENTS

| 6,495,154 | B1 | 12/2002 | Tam et al. ...................... 424/423 |
| 8,461,146 | B2 | 6/2013 | Seol et al. ..................... 514/217 |
| 2002/0037828 | A1 | 3/2002 | Wilson et al. ..................... 514/1 |
| 2002/0091129 | A1 | 7/2002 | Boolell ....................... 514/252.16 |
| 2005/0123609 | A1 | 6/2005 | Hirsh et al. ................... 424/464 |
| 2009/0118211 | A1* | 5/2009 | Drai ..................... A61K 9/1652 514/44 R |
| 2009/0311327 | A1* | 12/2009 | Roberts ................ A61K 9/2009 424/489 |
| 2011/0071138 | A1* | 3/2011 | Seol ..................... A61K 31/135 514/217 |

FOREIGN PATENT DOCUMENTS

| CA | 2840521 | 1/2013 | ............. A61K 31/55 |
| KR | 10-2009-0120423 | 11/2009 | ............... B62D 3/04 |

OTHER PUBLICATIONS

Shah Shrey et al., "Formulation and in Vitro Evalution of Sustained Release Tablets of Clomipramine Hydrochloride", Pharma Science Monitor, Jan. 1, 2012 (Jan. 1, 2012).
Desai Divyakant et al: "Formulation design, challenges, and development considerations for fixed dose combination (FDC) of oral solid dosage forms" Pharmaceutical Development and Technology, Informa Healthcare, US, vol. 18, No. 6, Nov. 1, 2013 (Nov. 1, 2013), pp. 1265-1276.
International Search Report (ISR) dated May 29, 2015 in PCT/KR2015/012969 published as WO 2015/102337.
Salonia, A., et al., (2002). "A prospective study comparing paroxetine alone versus paroxetine plus sildenafil in patients with premature ejaculation". *The Journal of Urology*, 168(6):2486-2489.

* cited by examiner

*Primary Examiner* — Ali Soroush
(74) *Attorney, Agent, or Firm* — Harness, Dickey & Pierce, P.L.C.

(57) ABSTRACT

The present invention provides a pharmaceutical formulation comprising clomipramine or its pharmaceutically acceptable salt (preferably, clomipramine hydrochloride) as the first active ingredient, and sildenafil or its pharmaceutically acceptable salt (preferably, sildenafil citrate) as the second active ingredient, wherein stability of clomipramine is improved, and a method for manufacturing this pharmaceutical formulation. In particular, the present invention provides a pharmaceutical formulation comprising the above two active ingredients and manufactured by using a wet granulation method, wherein stability of clomipramine is improved, and a method for manufacturing this pharmaceutical formulation.

6 Claims, No Drawings

PHARMACEUTICAL COMPOSITION CONTAINING CLOMIPRAMINE AND PREPARATION METHOD THEREFOR

CROSS-REFERENCE TO RELATED APPLICATIONS

This application is a national phase application of PCT Application No. PCT/KR2014/012969, filed on 29 Dec. 2014, which claims benefit of Korean Patent Application No. KR 10-2013-0168702 filed 31 Dec. 2013. The entire disclosures of the applications identified in this paragraph are incorporated herein by references.

FIELD

The present disclosure relates to a pharmaceutical formulation having improved stability, which comprises clomipramine or its pharmaceutically acceptable salt as the first active ingredient, and sildenafil or its pharmaceutically acceptable salt as the second active ingredient, and a method for manufacturing thereof. In particular, the present invention relates to a pharmaceutical formulation manufactured by a wet granulation method, and a method for manufacturing thereof.

BACKGROUND

Clomipramine or its pharmaceutically acceptable salt has been used for treating depression from before, and also has effects on treating or preventing ejaculation delayed (premature ejaculation).

When administering this clomipramine or its pharmaceutically acceptable salt, a side effect of erectile dysfunction may occur, and in order to improve this side effect of erectile dysfunction, studies about administering clomipramine or its pharmaceutically acceptable salt with sildenafil or its pharmaceutically acceptable salt are ongoing.

Furthermore, it was known that sildenafil or its pharmaceutically acceptable salt can be used for treating or improving premature ejaculation because it inhibits contraction of vas deferens, seminal vesicle, prostate and urethra, and shows induction of peripheral analgesia, increase of erection period, inhibition of central sympathetic autonomic nerve reaction. Thus, the present inventors assume that administrating clomipramine or its pharmaceutically acceptable salt and sildenafil or its pharmaceutically acceptable salt at the same time may be more effective to treat or improve premature ejaculation.

However, not much is known about problems which can occur when containing these ingredients in one formulation until now.

DISCLOSURE

Technical Problem

The present disclosure is designed to solve the problems of the related art, and therefore the present disclosure is directed to providing a pharmaceutical formulation comprising clomipramine or its pharmaceutically acceptable salt as the first active ingredient and sildenafil or its pharmaceutically acceptable salt as the second active ingredient together and improving various problems, and a method for manufacturing thereof.

The present disclosure is directed to providing a pharmaceutical composition having improved stability and comprising clomipramine or its pharmaceutically acceptable salt as an active ingredient, and a method for manufacturing thereof.

In particular, the present disclosure relates to a manufacturing method for improving stability of a pharmaceutical formulation comprising the above two active ingredients and manufactured by a wet granulation method, and a pharmaceutical formulation manufactured by the method.

These and other objects and advantages of the present disclosure may be understood from the following detailed description and will become more fully apparent from the exemplary embodiments of the present disclosure. Also, it will be easily understood that the objects and advantages of the present disclosure may be realized by the means shown in the appended claims and combinations thereof.

Technical Solution

First of all, the present inventors found that a wet granulation processing is preferred to secure mixing uniformity in a product because clomipramine or its pharmaceutically acceptable salt, in particular, clomipramine hydrochloride itself has bad fluidity. For example, when manufacturing a tablet comprising the clomipramine or its pharmaceutically acceptable salt as an active ingredient in mass production, manufacturing granule by the wet granulation method and then tableting a tablet by using the manufactured granule is preferred in terms of securing mixing uniformity and preferable hardness of the tablet. More specifically, when manufacturing a formulation by simple mixing without the wet granulation of the clomipramine (in particular, clomipramine hydrochloride), stability of the clomipramine can be sort of secured, but it is difficult for fast production due to increased content non-uniformity for each formulation, thereby difficult for mass production. Furthermore, in the case of a tablet, it is difficult to secure proper hardness when it is manufactured by simple mixing or a dry granulation method, and consequently, there is a disadvantage of adding a lot of excipients. However, when manufacturing the clomipramine granule first by the wet granulation method and then conducting following process for manufacturing a tablet, a capsule and the like from the granule, these problems could be solved.

However, when manufacturing granule comprising the clomipramine or its pharmaceutically acceptable salt and the sildenafil or its pharmaceutically acceptable salt by the wet granulation method using a solvent (water, ethanol, isopropanol, methanol and the like), the present inventors unexpectedly found a problem of stability reduction of clomipramine, and this problem could be effectively solved by the method of the present invention. Namely, the present invention provides a solution of the problem of stability reduction of the clomipramine in the pharmaceutical formulation such as a tablet, a capsule and the like, manufactured by using the wet granulation method.

Thus, first of all, the present invention provides a pharmaceutical formulation containing: (a) the clomipramine or its pharmaceutically acceptable salt; and (b) the sildenafil or its pharmaceutically acceptable salt, wherein the clomipramine and the sildenafil are separated from each other to block contact between the clomipramine and the sildenafil. In particular, the present invention provides a pharmaceutical formulation containing: (a) the clomipramine hydrochloride and (b) the sildenafil citrate, wherein the clomipramine hydrochloride and the sildenafil citrate are separated from each other to block contact between the clomipramine and the sildenafil. These effects of the present invention are clearer in the pharmaceutical formulation manufactured by a process of manufacturing granule by using the wet granulation method. Preferably, the pharmaceutical formulation is a tablet or a capsule manufactured through the wet granulation method.

In the present invention, the wet granulation method includes a method of i) manufacturing active ingredient-containing granule through a process of manufacturing paste mixture of an active ingredient and a pharmaceutically acceptable excipient (for example, a filler, a binder, a diluent, a disintegrant and the like) by using a solvent such as water, ethanol, isopropanol, methanol, methylene chloride and the like, alone or in combination, forming this paste as granule of proper size, and then drying this granule, ii) manufacturing granule through a process using a fluid bed granulator with the same ingredients, i.e., manufacturing granule by spraying a binder made of the solvent while fluidizing the ingredients in a fluid bed, and then drying the agglomerated mixed ingredients and crushing thereof, or iii) drying while manufacturing wet granule of the same ingredients with a high speed mixer, but not limited thereto. In the present invention, any process of manufacturing active ingredient granule by using a solvent (namely, the solvent is contacted to the active ingredient) can be considered as the wet granulation method.

In general, when developing a complex formulation, mixing two drugs together is common and economic, but when manufacturing a complex formulation of the clomipramine and the sildenafil using the wet granulation method, the clomipramine and the sildenafil should be contained separately from each other to block contact between the clomipramine and the sildenafil. In consideration of manufacturing cost, it is much uneconomic to manufacture the complex formulation containing the clomipramine and the sildenafil separately, but stability for mixing the clomipramine and the sildenafil is important to be able to ignore this problem of manufacturing cost.

The pharmaceutical formulation of the present invention is not limited to content of the clomipramine and the sildenafil, but it is preferred to contain the clomipramine of 4 mg to 36 mg (based on free base) and the sildenafil of 10 mg to 150 mg (based on free base) per pharmaceutical formulation, it is more preferred to contain the clomipramine of 9 mg to 27 mg and the sildenafil of 25 mg to 100 mg per pharmaceutical formulation, and it is most preferred to contain the clomipramine of 12 mg to 15 mg and the sildenafil of 25 mg to 100 mg per pharmaceutical formulation.

The clomipramine of the present invention may be clomipramine free base or its pharmaceutically acceptable salt. The pharmaceutically acceptable salt of clomipramine includes, but is not limited to, hydrochloride, nitrate, phosphate, sulfate, hydrobromide, hydroiodide, nitrite, acetate, lactate, citrate, malate, succinate, fumarate, maleate, tartrate, benzoate, phthalate, sulfate, pyrosulfate, bisulfate, sulfite, bisulfite, nitrate, phosphate and the like. In particular, effects of the present invention are much more preferable when using the clomipramine hydrochloride lacking in fluidity.

The sildenafil of the present invention may be sildenafil free base or its pharmaceutically acceptable salt. The pharmaceutically acceptable salt of sildenafil includes, but is not limited to, citrate, hydrochloride, hydrobromide, hydroiodide, sulfate, bisulfate, nitrate, phosphate, phosphate dibasic, acetate, fumarate, lactate, tartrate, succinate, benzoate, pamoate and the like. In the present invention, the sildenafil citrate is preferred.

Preferably, in a pharmaceutical formulation manufactured through a process of manufacturing the clomipramine or its salt in the form of granule by the wet granulation method, the present invention provides the pharmaceutical formulation mentioned above, which comprises a tablet or granule containing any one of the two active ingredients, (a) ingredient and (b) ingredient; and the other ingredient not contained in the tablet or the granule and coated on the outside of the tablet or the granule (for example, it is the (b) ingredient if the (a) ingredient is contained in the tablet or the granule). Herein, the pharmaceutical formulation may further comprise a coated layer for separation made of hydrophilic polymer film coating material between the tablet or the granule; and a layer containing the other ingredient on the outside of the tablet or the granule.

In the case of the complex formulation containing two drugs, it is preferred to contain the two drugs in one tablet in terms of patient compliance, and a tablet containing both of the clomipramine and the sildenafil without contacting each other can be manufactured by manufacturing a tablet containing any one ingredient of the clomipramine and the sildenafil (selectively forming a coated layer for separation with hydrophilic polymer) and then coating the tablet with the other ingredient together with an additive used as a coating material. However, because content of the sildenafil is higher than that of the clomipramine, the tablet containing the two drugs may more preferably be manufactured by manufacturing a tablet containing the sildenafil, selectively forming a coated layer for separation, and then additionally coating thereof with a coating solution containing the clomipramine.

A machine for coating a tablet may be any machine used for making a conventional film-coated tablet.

Preferably, in a pharmaceutical formulation manufactured through a process of manufacturing granule by the wet granulation method, the present invention provides a pharmaceutical formulation mentioned above, which is a multi-layered tablet consisting of the first layer comprising the (a) ingredient and the second layer comprising the (b) ingredient. In the multilayered tablet, a separation membrane or a separation layer made of hydrophilic polymer or non-hydrophilic polymer (for example, ethyl cellulose, ethylene-vinyl acetate copolymer, polyvinyl acetate, polymethacrylate, amino methacrylate copolymer and the like) may exist between the first layer and the second layer.

A multilayered tablet means a tablet having two or three separate layers manufactured by adding another granule to a pre-manufactured tablet and then additionally tableting thereof, or supplying different granules into a punch hole of a tableting machine one after the other. The contact between the clomipramine and the sildenafil can be prevented because the clomipramine and the sildenafil are contained in different layers in the multilayered tablet, respectively. Furthermore, in order to block even the minimum contact, a membrane or a layer for separation may exist between the clomipramine-containing layer and the sildenafil-containing layer.

Preferably, in a pharmaceutical formulation manufactured through a process of manufacturing the clomipramine or its salt in the form of granule by the wet granulation method, the present invention provides a pharmaceutical formulation mentioned above, which is a press-coated tablet consisting of a core tablet containing any one of the (a) ingredient and the (b) ingredient; and an exterior layer containing the other ingredient surrounding the core tablet. The present invention provides a pharmaceutical formulation wherein the core tablet is coated with hydrophilic polymer.

A press-coated tablet means a tablet manufactured by preparing a small tablet (the core tablet), putting the small tablet into a punch hole having some amount of granules, filling punch hole with granules, and then tableting them. In the press-coated tablet, stability of the two drugs can be improved because the clomipramine and the sildenafil are separately contained in the core tablet and the exterior layer surrounding the core tablet. Furthermore, it also can block even the minimum contact by coating the core tablet with the hydrophilic polymer.

In the present invention, the hydrophilic polymer may be, for example, hydroyxpropylmethylcellulose, hydroyxpropylcellulose, polyvinylalcohol, carboxymethylcellulose, polyvinylpyrrolidone, polyethyleneoxide, polyethyleneglycol, polyethylene-polypropylene copolymer, polyoxyethylene-polyoxypropylene copolymer, methacrylate (co)polymer and the like, but not limited thereto.

In a pharmaceutical formulation manufactured by a process comprising the wet granulation method, the present invention is also based on a surprising fact that if any one ingredient of the clomipramine or its salt and the sildenafil or its salt is first manufactured in the form of granule and then mixing thereof with the other ingredient, stability of the clomipramine can be improved. For example, the present invention is based on a surprising fact that if the sildenafil or its pharmaceutically acceptable salt is fist manufactured in the form of granule and then mixing thereof with the clomipramine or its pharmaceutically acceptable salt or with the second granule comprising the clomipramine or its pharmaceutically acceptable salt, stability of the complex formulation comprising the clomipramine and the sildenafil can be improved.

Thus, for example, the present invention provides a pharmaceutical formulation, preferably a tablet, wherein the sildenafil or its pharmaceutically acceptable salt is manufactured as granule and therefore contact with the clomipramine or its pharmaceutically acceptable salt is reduced. The granule may be coated with polymer, preferably hydrophilic polymer (for example, hydroyxpropylmethylcellulose, hydroyxpropylcellulose, polyvinylalcohol, carboxymethylcellulose, polyvinylpyrrolidone, polyethyleneoxide, polyethyleneglycol, polyethylene-polypropylene copolymer, polyoxyethylene-polyoxypropylene copolymer, methacrylate (co)polymer and the like) in order to further reduce contact with the clomipramine. Coating of the granule may be conducted by any machine if the machine can spray a coating solution after fluidizing raw material power or granule, and for example, a fluid bed coating machine can be used.

Furthermore, the present invention provides a method for manufacturing a tablet or a capsule comprising the sildenafil and the clomipramine, which comprises: a step (S1) of manufacturing granule comprising any one active ingredient of the sildenafil or its pharmaceutically acceptable salt (preferably, sildenafil citrate) or the clomipramine or its pharmaceutically acceptable salt (preferably, clomipramine hydrochloride); a step (S2) of mixing an active ingredient not used in the (S1) step with the granule of the (S1) step, or mixing granule comprising the active ingredient not used in the (S1) step with the granule of the (S1) step; and a step (S3) of tableting the mixture of the (S2) step (selectively, after mixing with another additional ingredient (for example, a lubricant, a disintegrant and the like)), or filling the mixture of the (S2) step into a capsule (selectively, after mixing with another additional ingredient (for example, a lubricant and the like)).

When manufacturing granule, stability of the clomipramine is rapidly reduced when mixing the two main ingredients, the sildenafil and the clomipramine, with a solvent, and this stability reduction problem can be improved by the method disclosed in the present invention.

The manufacturing method is very simple, and a sildenafil and clomipramine-containing tablet manufactured by this manufacturing method shows good stability while securing content uniformity of the active ingredients.

In the above manufacturing method, the binder for manufacturing granule containing the active ingredient may more preferably be povidone (polyvinylpyrrolidone) in terms of stability of the clomipramine.

Furthermore, the present invention is based on a surprising fact that even if the clomipramine or its pharmaceutically acceptable salt, in particular, granule comprising the clomipramine hydrochloride does not include a usual binder for giving binding force (for example, hydroyxpropylmethylcellulose, hydroyxpropylcellulose, polyvinylpyrrolidone, carboxymethylcellulose, sodium carboxymethylcellulose, calcium carboxymethylcellulose, pre-gelatinized starch and the like), it can have enough binding force as granule for tableting, and the usual binder negatively affects to stability of the clomipramine or its pharmaceutically acceptable salt.

Thus, more preferably, the present invention provides a pharmaceutical formulation and a tablet mentioned above, wherein a binder is not substantially used or included when manufacturing the clomipramine-containing granule, and a method for manufacturing thereof.

In the present invention, the term "not substantially used or included" means that the ingredient is included in an amount of 0.5 wt % or less, preferably 0.3 wt % or less, more preferably 0.1 wt % or less, most preferably 0.01 wt % or less, based on the total weight of a pharmaceutical composition.

Furthermore, the present invention is based on a surprising fact that in the case of a composition comprising the clomipramine or its pharmaceutically acceptable salt, in particular, clomipramine hydrochloride, corn starch and/or mannitol may preferably be used (more preferably mannitol) as an excipient, and sodium starch glycolate may preferably be used as a disintegrant.

Thus, more preferably, the present invention further provides a tablet and a method for manufacturing the tablet, wherein mannitol is used as an excipient and/or sodium starch glycolate is used as a disintegrant when manufacturing a clomipramine-containing composition.

Preferably, the present invention provides a clomipramine hydrochloride-containing tablet manufactured by manufacturing granule by the wet granulation method and then tableting thereof, wherein a binder is not substantially included, and more preferably, the tablet comprises corn starch and/or mannitol (more preferably, mannitol) as an excipient, and/or sodium starch glycolate as a disintegrant.

Advantageous Effects

In a pharmaceutical formulation comprising clomipramine and sildenafil and manufactured by a wet granulation method, the present invention provides a pharmaceutical formulation having improved stability of the clomipramine and a method for manufacturing thereof.

BEST MODE

Hereinafter, preferred embodiments of the present disclosure will be described in detail. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

MODE FOR DISCLOSURE

<Compatibility and Stability Evaluation Method>

Compatibility and stability of the following Examples and Comparative Examples were evaluated by increase and decrease of change on impurity using HPLC, and an impurity test method is as follows.

Impurity Test Method 15 mg of clomipramine hydrochloride was weighed, put into a 50 mL volume flask and dissolved in 0.01 N hydrochloric acid and then 0.01 N hydrochloric acid was added to adjust a marked line. The solution was filtered and used as a test solution. 15 mg of clomipramine hydrochloride standard was accurately weighed, put into a 50 mL volume flask and dissolved in 0.01 N hydrochloric acid and then 0.01 N hydrochloric acid was added to adjust a marked line. 10 mL of this solution was weighed and diluted with 0.01 N hydrochloric acid to make 100 mL, and 2 ml of the diluted solution was accurately weighed and diluted again with 0.01 N hydrochloric acid to make 100 mL. The final solution was used as a standard solution. Then, the standard solution was tested according to the following conditions, and average area of clomipramine hydrochloride peaks in the standard solution, ASC, and each unknown impurity peak area, $A_{IU}$, were calculated.

Each unknown impurity (%) =

$$\frac{A_{IU}}{A_{SC}} \times \frac{C_C \text{ (mg/mL)} \times 50 \text{ (mL)}}{\text{Displayed amount of clomipramine hydrochloride in one tablet (mg)}} \times P\ (\%)$$

Total impurity (%)=Sum of each unknown impurity (%)

$C_C$: Clomipramine hydrochloride concentration in standard solution (mg/mL)

P: Purity of clomipramine hydrochloride standard (%)

HPLC condition

Detector: UV spectrophotometer (detection wavelength: 270 nm)

Column: Cadenza CD-C18, 250×4.6 mm, 3 μm or equivalent column

Flow rate: 1.0 mL/min

Injection volume: 20 μL

Mobile phase: 625 mL of buffer was put into a 1000 mL volume flask, acetonitrile was added to adjust a marked line, and then the resulting solution was filtered to remove bubbles.

Buffer: 2.2 g of sodium 1-heptanesulfonate, 2 mL of glacial acetic acid and 4.0 mL of trimethylamine were dissolved in purified water and accurately adjusted to 1000 mL, and then pH was adjusted to 4.2±0.1 with phosphoric acid.

Storage Method

Storage container: HDPE bottle

Storage condition: Accelerated storage, 40±2° C./75±5% RH

<Test Example 1> Evaluation of Compatibility Between Main Ingredients

Sample Preparation Method

All ingredients except for a binder and a solvent were mixed according to the following Table 1, and in the case of a composition with a binder, the binder was dissolved in a solvent, and in the case of a composition without a binder, granulation was conducted with only a solvent, and then the granule was dried at 60° C. and oscillated to manufacture granule.

TABLE 1

| Purpose of Use | Ingredient | Amount (mg) | | | | |
|---|---|---|---|---|---|---|
| | | Example 1 | Example 2 | Example 3 | Example 4 | Example 5 |
| Main ingredient | Clomipramine hydrochloride | 15.00 | 15.00 | 15.00 | 15.00 | 15.00 |
| Main ingredient | Sildenafil citrate | 70.23 | 70.23 | — | — | — |
| Binder | Povidone | — | 3.00 | — | 0.50 | — |
| Binder | HPMC | — | — | — | — | 0.50 |
| Solvent | Purified water | Suitable amount | Suitable amount | Suitable amount | Suitable amount | Suitable amount |

Impurity Test Result

The granules were stored under the accelerated condition for four weeks and then impurity was evaluated. Results were shown in the following Table 2.

TABLE 2

| | Initial | | Acceleration 4 weeks | |
|---|---|---|---|---|
| Sample | Single max. | Total | Single max. | Total |
| Example 1 | 0.17 | 0.64 | 1.62 | 3.42 |
| Example 2 | 0.16 | 0.63 | 2.20 | 5.75 |
| Example 3 | 0.17 | 0.20 | 0.16 | 0.21 |
| Example 4 | 0.16 | 0.20 | 0.17 | 0.29 |
| Example 5 | 0.16 | 0.20 | 0.29 | 0.43 |

As shown in Table 2, when comparing Examples 1 and 2 containing both of the clomipramine hydrochloride and the sildenafil citrate as a main ingredient and Examples 3 and 4 not containing the sildenafil citrate, the amount of impurities in Examples 1 and 2 containing both of the two main ingredients was significantly increased during storage. Furthermore, initial results of Examples 1 and 2 showed higher impurity value than Examples 3 to 5 not containing the sildenafil citrate because impurity of the sildenafil citrate itself was added to the total impurity.

Furthermore, when comparing impurity increase during storage in Examples using povidone as a binder and Example 5 using HPMC as a binder, Example 4 using povidone rather than HPMC showed better stability.

Thus, it was decided that when manufacturing granule containing both of the clomipramine hydrochloride and the sildenafil citrate, a wet granulation method is not proper due to mutual influence between the two ingredients, and manufacturing the granule by containing the two ingredients separately is stabler. Furthermore, it was decided that when manufacturing the clomipramine hydrochloride granule by the wet granulation method, using povidone (PVP) as a binder rather than HPMC is proper for impurity stability occurring during storage.

<Test Example 2> Evaluation of Compatibility Between Main Ingredient and Excipient Sample Preparation Method According to the following Table 3, the clomipramine hydrochloride as a main ingredient and each excipient were sieved, mixed together, granulated with purified water, dried at 60° C. and then oscillated to manufacture granule.

TABLE 3

| | Amount (mg) | | | | |
|---|---|---|---|---|---|
| Ingredient | Example 6 | Example 7 | Example 8 | Example 9 | Example 10 |
| Clomipramine hydrochloride | 15 | 15 | 15 | 15 | 15 |
| Lactose | 135 | — | — | — | — |
| Microcrystalline cellulose | — | 135 | — | — | — |
| Corn starch | — | — | 135 | — | — |
| Sodium bicarbonate | — | — | — | 135 | — |
| Mannitol | — | — | — | — | 135 |
| Purified water | Suitable amount | Suitable amount | Suitable amount | Suitable amount | Suitable amount |

Impurity Test Result

Impurity test results were shown in the following Table 4.

TABLE 4

| | Initial | | Acceleration 4 weeks | |
|---|---|---|---|---|
| Sample | Single max. | Total | Single max. | Total |
| Example 6 | 0.17 | 0.30 | 0.53 | 1.77 |
| Example 7 | 0.16 | 0.27 | 0.37 | 1.54 |
| Example 8 | 0.15 | 0.22 | 0.16 | 0.45 |
| Example 9 | 0.16 | 0.23 | 0.36 | 1.65 |
| Example 10 | 0.16 | 0.30 | 0.16 | 0.27 |

As shown in the impurity test result in Table 4 for confirming compatibility between the main ingredients and the excipient, it was confirmed that initial impurity values were similar in all Examples, but Example 8 using corn starch and Example 10 using mannitol were stabler during accelerated storage.

Thus, it was found that when manufacturing the clomipramine hydrochloride granule by the wet granulation, corn starch and mannitol are stable against impurity production during storage, and mannitol is stabler than corn starch.

<Test Example 3> Evaluation of Compatibility Between Main Ingredient and Binder

Sample Preparation Method

According to the following Table 5, the clomipramine hydrochloride as a main ingredient and each excipient were sieved, mixed together. Povidone was separately dissolved in purified water to make a binder solution (if there was no binder, purified water was used as a binder solution) and added to the mixture. The resulting solution was granulated, dried at 60° C. and then oscillated to manufacture granule.

TABLE 5

| | Amount (mg) | | | |
|---|---|---|---|---|
| Ingredient | Example 8 | Example 11 | Example 10 | Example 12 |
| Clomipramine hydrochloride | 15 | 15 | 15 | 15 |
| Corn starch | 135 | 135 | — | — |
| Mannitol | — | — | 135 | 135 |
| Povidone | — | 6 | — | 6 |
| Purified water | Suitable amount | Suitable amount | Suitable amount | Suitable amount |

Impurity Test Result

Impurity test results were shown in the following Table 6.

TABLE 6

| | Initial | | Acceleration 4 weeks | |
|---|---|---|---|---|
| Sample | Single max. | Total | Single max. | Total |
| Example 8 | 0.15 | 0.22 | 0.16 | 0.45 |
| Example 11 | 0.16 | 0.34 | 1.28 | 5.27 |
| Example 10 | 0.16 | 0.30 | 0.16 | 0.27 |
| Example 12 | 0.16 | 0.28 | 0.86 | 3.06 |

According to Table 6 evaluating compatibility between the clomipramine hydrochloride as a main ingredient and the binder (povidone) in Example 1 and the excipient in Example 2, Example 12 containing mannitol showed better storage stability than Example 11 containing corn starch. However, when compared with Examples 8 and 10 not containing the binder, it was confirmed that the case containing the binder showed worse storage stability. Furthermore, it was confirmed that even if the binder is not used, the granule containing the clomipramine hydrochloride had enough binding force.

Thus, when manufacturing the clomipramine hydrochloride granule by the wet granulation method, manufacturing granule without the binder, which affects to stability during manufacture, showed better storage stability.

<Test Example 4> Evaluation Compatibility Between Main Ingredient and Disintegrant Sample Preparation Method According to the following Table 7, the clomipramine hydrochloride as a main ingredient and each excipient were sieved, mixed together, granulated with purified water, dried at 60° C. and then oscillated to manufacture granule.

TABLE 7

| | Amount (mg) | |
|---|---|---|
| Ingredient | Example 13 | Example 14 |
| Clomipramine hydrochloride | 15 | 15 |
| Mannitol | 175 | 175 |
| Crosscarmellose sodium | 10 | — |
| Sodium starch glycolate | — | 10 |
| Purified water | Suitable amount | Suitable amount |

Impurity Test Result

Impurity test results were shown in the following Table 8.

TABLE 8

| | Initial | | Acceleration 4 weeks | |
|---|---|---|---|---|
| Sample | Single max. | Total | Single max. | Total |
| Example 13 | 0.16 | 0.29 | 0.67 | 1.57 |
| Example 14 | 0.16 | 0.28 | 0.16 | 0.29 |

Impurity test results for storage stability of Examples 13 and 14 manufactured by using crosscarmellose sodium and sodium starch glycolate as a disintegrant as shown in Table 7 were shown in Table 8. As can be confirmed in Table 8, it was confirmed that Example 14 using sodium starch glycolate showed better storage stability.

<Test Example 5> Sample Preparation and Stability Evaluation

Sample Preparation Method

Example 15 [Manufacture of Clomipramine Hydrochloride Single Tablet]

Clomipramine hydrochloride, mannitol, pregelatinized starch and sodium starch glycolate of quantity as shown in the following Table 9 were sieved through a 30 mesh sieve and mixed together. This mixture was granulated with purified water, dried at 60° C. and then oscillated to manufacture clomipramine hydrochloride granule. Magnesium stearate was added to the granule, post-mixed, and then tableted according to a general method for manufacturing a tablet.

Example 16 [Manufacture of Clomipramine Hydrochloride Granule, Sildenafil Citrate Granule and Complex Tablet of Clomipramine Hydrochloride and Sildenafil Citrate]

Clomipramine hydrochloride granule was manufactured with quantity as shown in the following Table 9 by the same method with Example 15. Separately, sildenafil citrate, microcrystalline cellulose, anhydrous dibasic calcium phosphate and crosscarmellose sodium were sieved through a 30 mesh sieve and mixed together. This mixture was granulated with a binder solution manufactured by dissolving povidone in purified water, dried at 60° C. and then oscillated to manufacture sildenafil citrate granule. Magnesium stearate was mixed with the clomipramine hydrochloride granule and the sildenafil citrate granule, and then tableted according to a general method for manufacturing a tablet.

Example 17 [Manufacture of Sildenafil Citrate Granule and Complex Tablet by Post-Mixing of Clomipramine Hydrochloride]

Sildenafil citrate granule was manufactured with quantity as shown in the following Table 9 by the same method with Example 16. Clomipramine hydrochloride was mixed with the granule, and then magnesium stearate was also mixed therewith, and then tableted according to a general method for manufacturing a tablet.

TABLE 9

| | Amount (mg) | | |
|---|---|---|---|
| Ingredient | Example 15 | Example 16 | Example 17 |
| Clomipramine hydrochloride | 15.00 | 15.00 | 15.00 |
| Sildenafil citrate | — | 70.23 | 70.23 |
| Mannitol | 151.00 | 151.00 | — |
| Microcrystalline cellulose | — | 57.28 | 57.58 |
| Anhydrous dibasic calcium phosphate | — | 52.19 | 52.19 |
| Pregelatinized starch | 20.00 | 20.00 | — |
| Sodium starch glycolate | 12.00 | 12.00 | — |
| Crosscarmellose sodium | — | 12.00 | 12.00 |
| Povidone | — | 6.00 | 6.00 |
| Magnesium stearate | 2.00 | 4.00 | 2.00 |
| Purified water | Suitable amount | Suitable amount | Suitable amount |
| Total weight (mg) | 200.0 | 400.0 | 215.0 |

Impurity Test Result

Impurity test results were shown in the following Table 10.

TABLE 10

| | Initial | | Acceleration 4 weeks | |
|---|---|---|---|---|
| Sample | Single max. | Total | Single max. | Total |
| Example 15 | 0.15 | 0.20 | 0.16 | 0.21 |
| Example 16 | 0.15 | 0.59 | 0.16 | 0.60 |
| Example 17 | 0.09 | 0.55 | 0.09 | 0.58 |

As the results of the above Table 10, significant change on stability during storage was not observed in Examples 15, 16 and 17 compared to initial. The reason why the initial values of Examples 16 and 17 were higher than Example 15 is considered that the impurity values of the sildenafil citrate itself contained in Examples 16 and 17 were added to the total impurity calculation.

Thus, it was confirmed that a pharmaceutical formulation comprising two active ingredients and having improved stability can be manufactured by just a wet granulation method. Specifically, stability of the stabilized clomipramine hydrochloride granule was maintained even if manufacturing a complex formulation containing the sildenafil citrate with the manufactured granule. Furthermore, it was confirmed that stability was maintained even if manufacturing the sildenafil citrate granule and then manufacturing a mixture by just mixing the clomipramine hydrochloride to the granule, not by the wet granulation method.

<Test Example 6> Stability Evaluation of Tablet Containing Fluid Bed Granule

Sample Preparation Method

Example 18

Sildenafil citrate, mannitol, microcrystalline cellulose, anhydrous dibasic calcium phosphate, pregelatinized starch, sodium starch glycolate and crosscarmellose sodium of quantity as shown in the following Table 11 were sieved through a 30 mesh sieve, mixed together, and then put into a fluid bed machine. A binder solution manufactured by dissolving clomipramine hydrochloride and povidone in purified water was sprayed to the mixture in the fluid bed machine to manufacture granule. The manufactured granule was sieved through a 30 mesh sieve, mixed with magnesium stearate, and then tableted according to a general method for manufacturing a tablet.

Example 19

Lactose hydrate, pregelatinized starch and sodium starch glycolate of quantity as shown in the following Table 11 were sieved through a 30 mesh sieve, mixed together, and then put into a fluid bed machine. A binder solution manufactured by dissolving the clomipramine hydrochloride and povidone in purified water was sprayed to the mixture in the fluid bed machine to manufacture granule. The manufactured granule was sieved through a 30 mesh sieve, mixed with magnesium stearate, and then tableted according to a general method for manufacturing a tablet.

TABLE 11

| | Amount (mg) | |
|---|---|---|
| Ingredient | Example 18 | Example 19 |
| Clomipramine hydrochloride | 15.00 | 15.00 |
| Sildenafil citrate | 70.23 | — |
| Mannitol | 151.00 | — |
| Microcrystalline cellulose | 57.28 | — |
| Lactose hydrate | — | 111.5 |
| Anhydrous dibasic calcium phosphate | 52.19 | — |
| Pregelatinized starch | 20.00 | 14.5 |
| Sodium starch glycolate | 12.00 | 3.0 |
| Crosscarmellose sodium | 12.00 | — |
| Povidone | 6.00 | 4.5 |
| Magnesium stearate | 4.00 | 1.5 |
| Purified water | Suitable amount | Suitable amount |
| Total weight (mg) | 400.0 | 150.0 |

Results of impurity test conducted by the same method used previously were shown in the following Table 12.

TABLE 12

| | Initial | | Acceleration 4 weeks | |
|---|---|---|---|---|
| Sample | Single max. | Total | Single max. | Total |
| Example 18 | 0.11 | 0.45 | 0.16 | 1.03 |
| Example 19 | 0.15 | 0.22 | 0.14 | 0.25 |

As the results of the above Table 12, it was confirmed that total impurity of Example 18 containing both of the clomipramine hydrochloride and the sildenafil citrate was increased more than Example 19 containing only the clomipramine hydrochloride even if manufacturing granule by fluid bed. Thus, it was confirmed that, in the case of wet granule using a solvent, impurity was increased when contacting the clomipramine hydrochloride and the sildenafil citrate with the solvent.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A method for manufacturing a pharmaceutical formulation comprising sildenafil and clomipramine, comprising:
    (S1) manufacturing granules comprising clomipramine or its pharmaceutically acceptable salt by a wet granulation method;
    (S2) mixing the granules of the (S1) step with granules comprising sildenafil or its pharmaceutically acceptable salt; and
    (S3) tableting the mixture of the (S2) step, wherein the pharmaceutical formulation is in a tablet form.

2. The method of claim 1, wherein the pharmaceutical formulation comprises clomipramine hydrochloride and sildenafil citrate.

3. The method of claim 1, wherein the granule comprising the sildenafil or its pharmaceutically acceptable salt comprises povidone.

4. The method of claim 1, wherein the granule comprising the clomipramine or its pharmaceutically acceptable salt does not substantially contain a binder.

5. The method of claim 1, wherein the granule comprising the clomipramine or its pharmaceutically acceptable salt comprises mannitol.

6. The method of claim 1, wherein the granule comprising the clomipramine or its pharmaceutically acceptable salt comprises sodium starch glycolate.

* * * * *